(12) United States Patent
Sapiens et al.

(10) Patent No.: US 12,268,447 B2
(45) Date of Patent: Apr. 8, 2025

(54) MEANS AND METHODS OF MEASURING REFRACTION

(71) Applicant: EyeQue Inc., Newark, CA (US)

(72) Inventors: Noam Sapiens, Newark, CA (US); John Serri, Newark, CA (US)

(73) Assignee: EyeQue Inc., Newark, CA (US)

( * ) Notice: Subject to any disclaimer, the term of this patent is extended or adjusted under 35 U.S.C. 154(b) by 845 days.

(21) Appl. No.: 17/378,063

(22) Filed: Jul. 16, 2021

(65) Prior Publication Data

US 2021/0338077 A1 Nov. 4, 2021

Related U.S. Application Data

(63) Continuation-in-part of application No. 17/223,944, filed on Apr. 6, 2021, now Pat. No. 12,114,927, which is a continuation-in-part of application No. 16/809,482, filed on Mar. 4, 2020, now Pat. No. 11,503,997, which is a continuation-in-part of application No. 16/685,017, filed on Nov. 15, 2019, now Pat. No. 11,484,195, which is a continuation-in-part of application No. 16/276,302, filed on Feb. 14, 2019, now Pat. No. 10,588,507, which is a continuation-in-part of application No. 15/491,577, filed on Apr. 19, 2017, now Pat. No. 9,844,962.

(60) Provisional application No. 63/052,644, filed on Jul. 16, 2020, provisional application No. 62/409,276, filed on Oct. 17, 2016.

(51) Int. Cl.
*A61B 3/103* (2006.01)
*A61B 3/135* (2006.01)

(52) U.S. Cl.
CPC .............. *A61B 3/103* (2013.01); *A61B 3/135* (2013.01)

(58) Field of Classification Search
CPC ............ A61B 3/103; A61B 3/135; A61B 3/10
USPC ......................................... 351/205
See application file for complete search history.

(56) References Cited

U.S. PATENT DOCUMENTS

| | | | | |
|---|---|---|---|---|
| 2002/0088940 A1* | 7/2002 | Watanabe | ............. | H01J 37/224 250/310 |
| 2003/0132372 A1* | 7/2003 | Lofthus | ................ | G02B 26/127 250/234 |
| 2013/0222764 A1* | 8/2013 | Thompson | ............... | A61B 3/18 351/209 |
| 2016/0047710 A1* | 2/2016 | Maeda | ............... | G01M 11/0271 356/512 |

* cited by examiner

*Primary Examiner* — Mohammed A Hasan
(74) *Attorney, Agent, or Firm* — Steven A. Nielsen; www.NielsenPatents.com

(57) ABSTRACT

In an embodiment, multiple conjugate planes are used to create a plurality of optical pupil planes and a plurality of image planes. These optical planes solve multiple problems and introduce significant performance enhancements in the system. In one implementation of a disclosed embodiment, the measurement channel is based on the reverse Shack-Hartmann principle. By introducing a relay system (for example a 4-f lens system) the slit plane could be made conjugate to the measured system pupil plane (unlike a previous implementation where the slits were places away from the pupil plane as it was not accessible directly). Creating a virtual pupil plane allows for more accurate placement of the plane without the need for contact with the measured optical system.

9 Claims, 14 Drawing Sheets

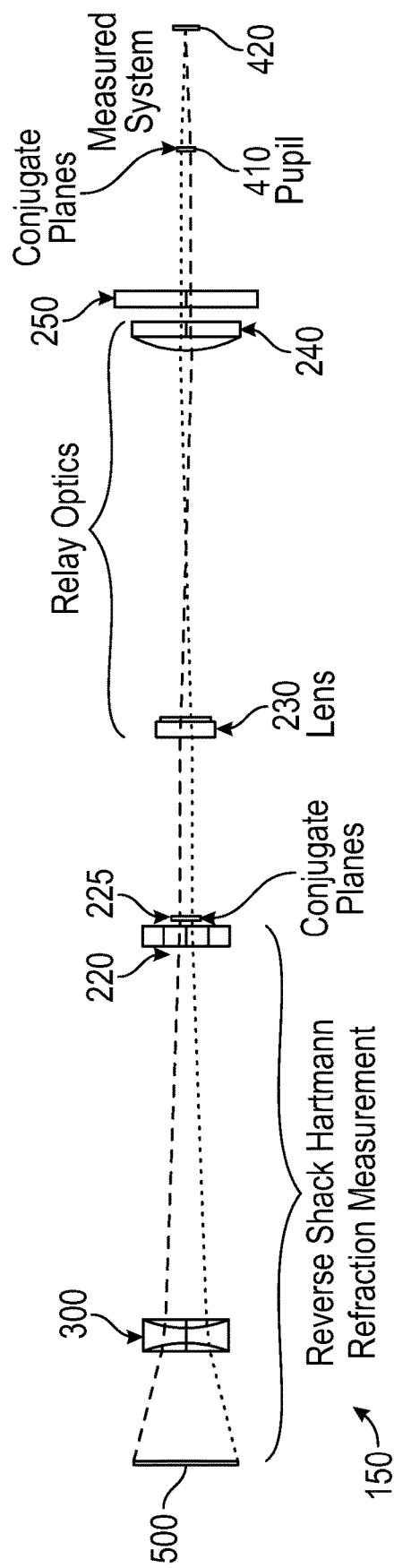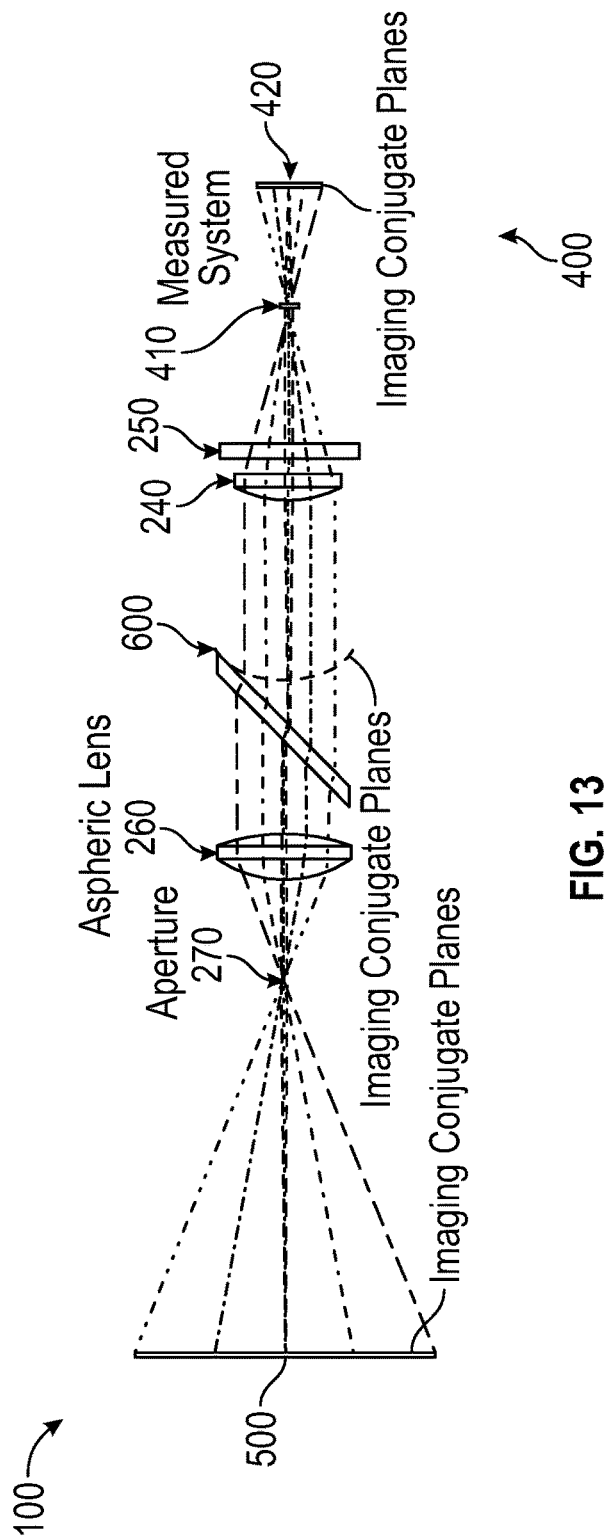
FIG. 12
FIG. 13

MEANS AND METHODS OF MEASURING REFRACTION

CROSS-REFERENCE TO RELATED APPLICATIONS

This utility application is a Continuation in Part or CIP of and claims the benefit and priority dates of the following patent applications, Ser. No. 17/223,944 filed on Apr. 6, 2021 which is a CIP of Ser. No. 16/809,482 filed on Mar. 4, 2020 which is a CIP Ser. No. 16/685,017 filed on Nov. 15, 2019 which is a CIP of Ser. No. 16/276,302 filed on Feb. 14, 2019 now U.S. Pat. No. 10,588,507 which is a CIP of Ser. No. 15/491,577 filed on Apr. 19, 2017, now U.S. Pat. No. 10,206,566 which claims the priority of provisional patent application 62/409,276 filed on Oct. 17, 2016. This utility application claims the benefit and priority date of U.S. application 63/052,644 filed on Jul. 16, 2020. The contents of the priority patent applications and patents are hereby incorporated herein by referenced as if restated in their entirety herein. The patent applications and patents described above are sometimes referred to herein as "the related applications."

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

Vision is arguably the most important of the senses. The human eye and its direct connection to the human brain is an extremely advanced optical system. Light from the environment goes through the eye optical train comprised of the cornea, the pupil, and the lens and focuses to create an image on the retina. As all optical systems, light propagation through the eye optics is subject to aberrations. The most common forms of aberrations in the eye are defocus and astigmatism. These low order aberrations are the cause of the most common refractive eye conditions myopia (near-sightedness) and hyperopia (farsightedness). Higher order aberrations are also present and can be described most conveniently by the Zernike polynomials. These usually have a lower effect on visual function. The eye, like any other organ in the human body, may suffer from various diseases and disorders, the most prominent today are: cataract, AMD, glaucoma, diabetic retinopathy, dry eye. Other conditions exist and should also be considered in the scope of this application.

Ophthalmic measurements are critical for eye health and proper vision. Those ophthalmic measurements could be sectioned into objective and subjective types. Objective types measurements give a metric of a physiological, physical (e.g. mechanical or optical), biological or functional without the need for input from the measured individual (patient, subject, user or consumer). Examples of objective tests include but are not limited to OCT (optical coherent tomography used to image a 3 dimensional and cross sections of the eye), scanning laser ophthalmoscope (SLO, used for spectral imaging of the retina), fundus image (used to present an image of the retina), auto-refractor (used for refraction measurement), keratometer (used for providing a profile of the cornea), tonometer (used to measure the IOP—intra ocular pressure). Subjective measurements give a metric with relation to the individual input. That is, they provide parameters that also take into consideration the brain functions, perception and cognitive abilities of the individual. Examples of subjective tests include but are not limited to visual acuity test, contrast sensitivity test, phoropter refraction test, color vision test, visual field test, and the EyeQue PVT and Insight.

Today, both objective and subjective eye exams (measurements) are done by an ophthalmologist or an optometrist. The process usually involves the patient needing to schedule an appointment, wait for the appointment, travel to the appointment location (e.g. office or clinic), wait in line, perform multiple tests using various tools and potentially moving between different technicians and different eye doctors. The prolonged wait times both for the appointment as well as in line at the appointment location, along with the hassle of performing the tests with different professionals and the duration of those tests might seem daunting to many patients. Furthermore, the shear effort associated with the process and even the requirement of remembering to start the process to begin with might deter patients from going through with it.

Moreover, currently about 2.5 billion people do not have access to eye and vision care at all. The cost of eye exams could be considered quite significant especially in some places in the world. This poses a hindrance to the availability of eye care in third world countries for example. The cost, time consumption and perceived hassle also makes repeated eye exams, at times/prohibitive, especially at the desired frequency. More frequent eye exams might be necessary in special cases (for example after refractive surgery or cataract surgery where repeated measurements should be performed to track the progress of the patient's status over time and the success of the surgery. Additionally, even under normal circumstances, measurements at a doctor's office only represent a single point in time. The situation under which the measurements were made might not be optimal or do not fully represent the patient's characteristics. The patient might have been tired, stressed or agitated (a doctor's visit might be quite stressful in and of itself but could also being run from test to test and being posed with questions and options elevate the patient's level of stress) or was just in a bad mood. Even the state of mind of the doctor themselves might influence the way the measurement is performed. Beyond all that, the time of day and other environmental conditions (whether direct e.g. lighting conditions or indirect e.g. temperature) could also affect the measurement and provide incomplete or false information.

The availability of information (including specifically medical information) on the Internet, the increased awareness of people for preventive medicine, and the emergence of tele-medicine leads to many taking control of their own health. Devices for screening, monitoring and tracking medical conditions are quite pervasive in today's world, for example blood pressure measurement devices, and blood sugar monitors. The technological advancements allow for people to be more independent in diagnosis, prevention and tracking of various health conditions. Furthermore, many prefer to perform these activities in the comfort of their homes without the need for appointments or other time-consuming activities. In case of an anomaly, they would call or email their physicians to consult for the appropriate course of action.

The advancement of technologies effectively makes computers with screens and cameras ubiquitous in the form of laptops, tablets and smartphones. Therefore, enabling many people to have a device already capable of computing displaying and recording information.

All this brings the need for a series of devices that will enable users to perform ophthalmic measurements at home, by themselves, in a timely and cost-effective manner. It should be clear that the quality of these measurements and their accuracy and precision should meet or exceed the standards of today's measurement methods.

This vision could be further enhanced by use of cloud-based data and analytics that enables complete access to the entire history of a patient exams, tests and measurements. Moreover, the use of artificial intelligence (AI) will enable diagnosis based on machine learning and big data. This could be done by means of data mining, neural network decision making and pattern detection and recognition, as some examples of the AI capabilities.

To summarize, the vision for eye care in the not so far future will look like: A complete solution for eye and vision care for consumers and doctors; Remote, self-administered battery of tests for both disease and functional; measurements are enabled by technology and devices, AI is used for analysis, tracking and reporting. Enhanced by big data correlations and insights.

In simple terms, as an example: A person sits on their couch at the comfort of their home, uses a device to do various measurements, that data is uploaded to an AI for analysis. The AI will let the person know the results and notify the doctor. The AI will initiate alerts for the person and doctor in necessary cases. The person will not need to get up unless a serious issue occurs (i.e. surgery). All other issues will be dealt with remotely (e.g. email/phone/video conference with the doctor, order glasses and have them delivered to the home, direct delivery of doctor prescribed medications).

Despite the apparent approach of "direct to consumer", the methodologies could easily be implemented for a more enterprise like model. One example of such implementation will have a hierarchical structure in which an entity such as a hospital, association, or a medical insurance company provides the ability for the doctors to provide their patients with such devices and capabilities. The devices are all connected through the user accounts to the cloud and the measurements are streamed directly into the users' accounts (and potentially their medical records). Those accounts could be attached to one or more doctors and can also be transferred and shared.

(1) FIELD OF THE INVENTION

The invention generally relates to refraction measurement systems. More particularly, the invention relates to means and methods of performing a refraction measurement of an optical system using the reverse Shack-Hartmann. Refraction measurement of an optical system is usually done by means of expensive equipment such as automatic refractometer or interferometer for scientific and industrial systems or by means of an eye exam by an optometrist if the optical system is the human eye. The refraction measurement by the optometrist usually consists of an auto-refractor measurement and a phoropter test. The auto-refractor lacks the accuracy required for the measurement for multiple reasons, e.g. measurement noise and the perception input of the person. The phoropter test is not really a refraction measurement as it is a completely subjective test taking the best corrected visual acuity as the sole criteria for the person's refraction. A reverse Shack-Hartmann refraction measurement is an actual measurement of the optical system refraction while taking into consideration the subjective, perception-based input of the person taking the test into consideration thus giving results that are the best of both worlds. The reverse Shack-Hartmann principle is extensively described in [Ser. No. 16/276,302; 10,206,566; 15/491,557; 62776041]. For reference, the method includes the presentation of multiple patterns through multiple optical elements and the measured optical system and performing an alignment of these multiple patterns to a specific configuration that corresponds to a known refraction value for the measured system. The measurement is subjective to the measured system in that the pattern alignment is specific to that particular system and corresponds to its refraction state.

(2) DESCRIPTION OF THE RELATED ART

The known related art fails to anticipate or disclose the principles of the present invention.

In the related art, refraction measurements that are based on the reverse Shack-Hartmann method have some significant disadvantages. The measurement usually requires multiple subjective alignment operations through the measured optical system. The measurement requires the field of view (FoV) to be small to allow for the required accuracy and optical alignment. In the case where the measured optical system is the human eye and as the measurement is subjective in nature and patterns are presented without any reference for depth the measurement is expected to be contaminated by variations in the optical power of the eye due to the accommodation effect. Essentially, the measurement cannot distinguish between the inherent refractive state of the eye and the measured refractive state that is composed of the inherent state with the addition of accommodation offset. The accommodation in these measurements cannot be controlled as either the measurement is monocular and causes a stereoscopic disparity for the subject as the images presented to each eye are different. In the case the device is binocular proper stimulus cannot be presented due to the FoV limitation of the devices.

In a somewhat related field, the small FoV of the system also reduces the capability of the system to integrate the performance other vision tests such as visual acuity or FoV test for example. The measurement systems that are currently available are made of only 2 optical paths for the measurement and use chromatic or baffle separation that do not allow for more than the measurement patterns to be presented.

In a previously presented implementation [PVT3 CIP patent application], the required tolerances for aligning of the different channels in the device are extremely tight and cause manufacturability issues. The effect of such misalignments is significant in terms of the accuracy of the refraction measurement. This is due to the asymmetric nature of the implementation.

Thus, there is a long felt need in the art for the present invention.

BRIEF SUMMARY OF THE INVENTION

The present invention overcomes shortfalls in the related art by presenting an unobvious and unique combination and configuration of methods and components to measure refraction of an optical system while allowing for an imaging channel to be overlaid optically.

The invention overcomes shortfalls in the related art by using a reverse Shack-Hartmann refraction measurement devices such as the devices disclosed in the priority applications and patents described above in conjunction with an imaging channel combined optically for example by means of a beam splitter.

In an embodiment of the invention, a refraction measurement device is comprised of a measurement channel and an imaging channel. The measurement channel is optically overlaid on the imaging channel allowing for a single image through the measured system. In one implementation of the proposed embodiment, the refraction measurement device is monocular. In that case a single measurement channel is attached to a single imaging channel and they are optically overlayed upon each other. In another implementation of the invention, the measurement is monocular while the device is binocular. In this case the measurement channel measures one portion of the optical system (e.g. human eye) while the imaging channel is aimed at another portion of the optical system (the other eye in previous example). In case of the human eyes as the optical system, this implementation relies on the visual combination in the brain from the two eyes to create a single coherent image in the brain without disparity.

In an embodiment of the invention, a binocular device is used to measure the refraction of the human eye. In an implementation of the device, a single measurement channel is used while two imaging channels are present, one for each eye. The measurement channel could be directed to each of the eyes by means of a mirror. The mirror could be turning, flipping, or two mirrors could be alternating by means of a linear motion drive (e.g. solenoid or motor and lead screw). In an alternative implementation of the invention, each imaging channel also has its own measurement channel. This implementation overcomes the challenge of optical variation due to different pupillary distances.

In an embodiment of the invention multiple conjugate planes are used to create a plurality of optical pupil planes and a plurality of image planes. These optical planes solve multiple problems and introduce significant performance enhancements in the system. In one implementation of the proposed embodiment, the measurement channel is based on the reverse Shack-Hartmann principle. By introducing a relay system (for example a 4-f lens system) the slit plane could be made conjugate to the measured system pupil plane (unlike the previous implementation where the slits were places away from the pupil plane as it was not accessible directly). Creating a virtual pupil plane allows for more accurate placement of the plane without the need for contact with the measured optical system. Furthermore, it increases the field of view of the measurement channel by utilizing the full NA of the system without obscuration. Working with conjugate planes also improves optical performance such as spot size. In another implementation of the proposed embodiment, the imaging channel utilizes a secondary, virtual imaging plane. The plane is created by an aspheric lens placed in front of the source screen. The plane generates a telecentric counterpart of the image on the screen with the appropriate field curvature to compensate for non-paraxial optical aberrations. The generated virtual point source plane transfers the flat screen image onto the curved retina of a human eye or any paraxially corrected optical system. In yet another implementation of the embodiment, the measurement channel and imaging channel are combined optically and may use the same optical element as the second element of the relay lens in the measurement channel and the Fourier transfer element to pupil plane in the imaging channel.

In an alternative embodiment of the invention the binocular device may be used as a virtual reality device or as a media viewing device used for watching TV, streaming content or playing games. The device allows for these functions without the requirement for the use of corrective lenses despite potential refractive error. This is done by controlling the depth of focus of the imaging channels in the device and accommodating the full range of expected refraction errors.

In an embodiment of the invention, the device is part of a complete system that includes the refraction measurement device, a gateway device that runs a user interface application and communicates with the device, and a back-end system that provides the required support, storage, reporting and calculation for the system.

In one disclosed process, a user logs into an account though a gateway application. The user then connects to the refraction measurement device. The user configures the device and the desired experience on the gateway application. The gateway application then communicates the information to the refraction measurement device. The user then performs the test on the refraction measurement device. The refraction measurement device then communicates with the gateway and/or the back-end to provide information and results for further analysis.

These and other objects and advantages will be made apparent when considering the following detailed specification when taken in conjunction with the drawings.

Figure 1:
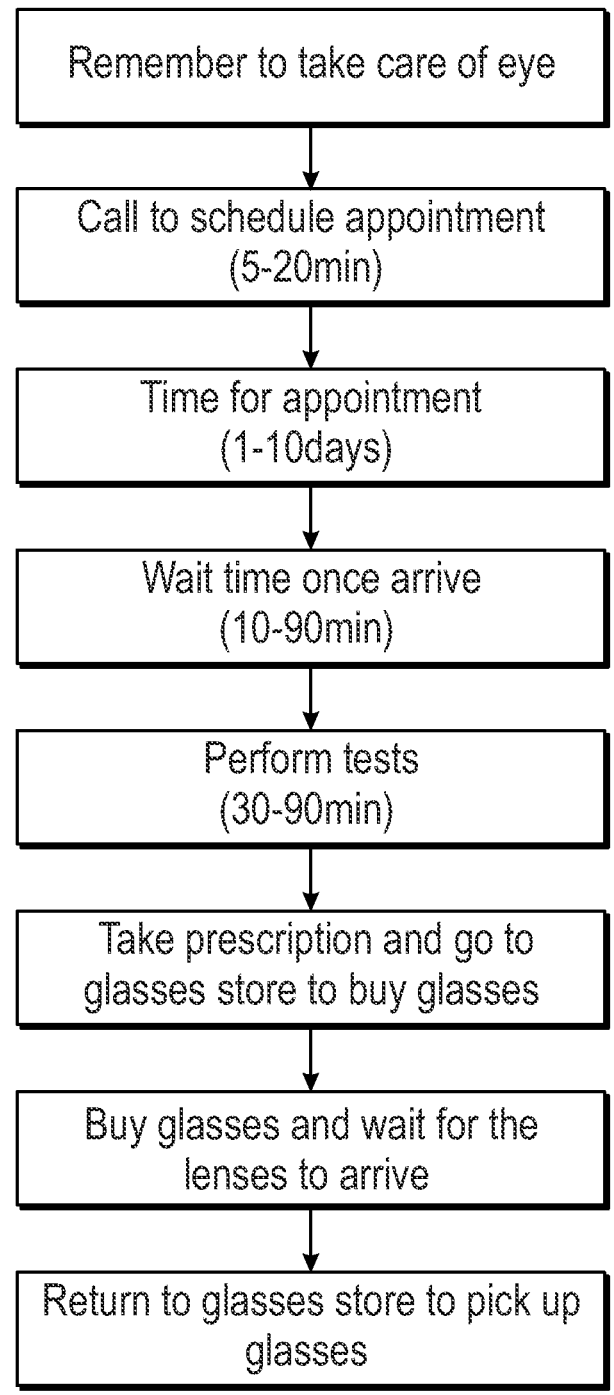
FIG. 1 Current process for obtaining eyeglasses
FIG. 2 Proposed example of process for obtaining eyeglasses
FIG. 3 Example of proposed enterprise model
FIG. 4 General concept of channel implementation of the invention
FIG. 5 Example monocular implementation of the invention
FIG. 6 Example monocular measurement with binocular device
FIG. 7 Example of monocular measurement and monocular imaging with relay
FIG. 8 Example of monocular measurement and monocular imaging without relay
FIG. 9 Example binocular device with single measurement channel
FIG. 10 Example binocular device with dedicated measurement channels
FIG. 11 Example screen implementation
FIG. 12 Proposed example measurement channel design
FIG. 13 Proposed example imaging channel design
FIG. 14 Proposed example combined system design
FIG. 15 Optical design for AR/VR system
FIG. 16 Example device connectivity architecture
FIG. 17 Example flow diagram of device use
Figure 2:
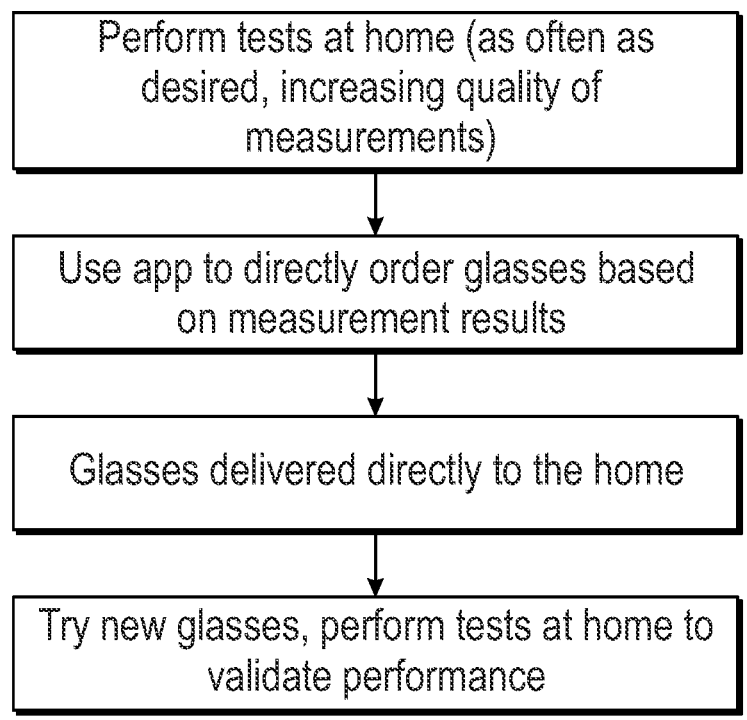
Figure 3:
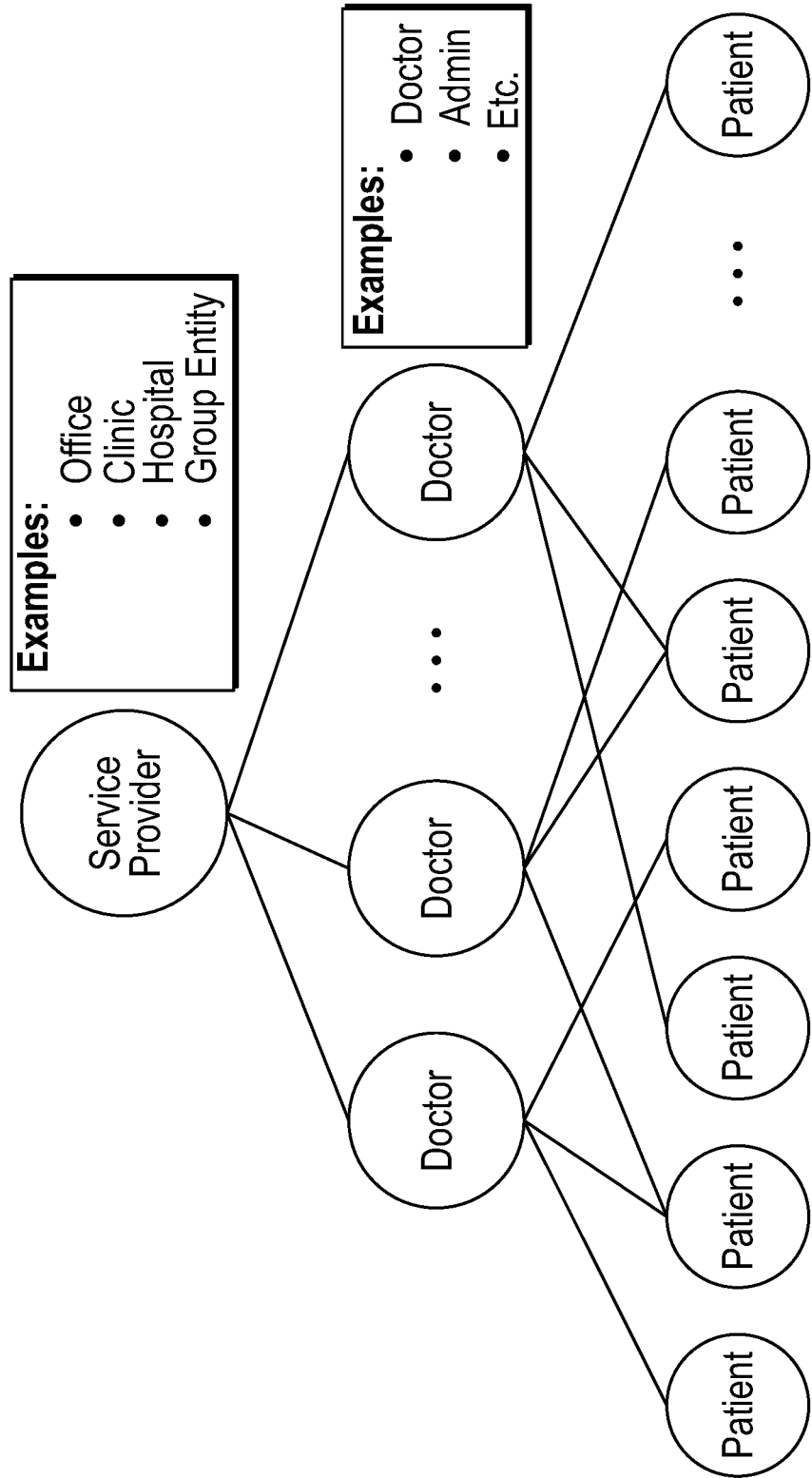

REFERENCE NUMERALS IN THE DRAWINGS 100 a disclosed imaging channel general
150 a disclosed measurement channel
200 demagnification lens
220 pair of colored lenses
225 slit plane
230 lens, sometime a first relay lens
240 convex lens, sometimes a relay optic
250 window 260 aspheric lens
270 aperture
400 measured optical system
410 pupil of a measured optical system
420 image plane of a measured optical system
500 screen
600 beam splitter
700 combined imaging channel and measurement channel

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

Figure 4:
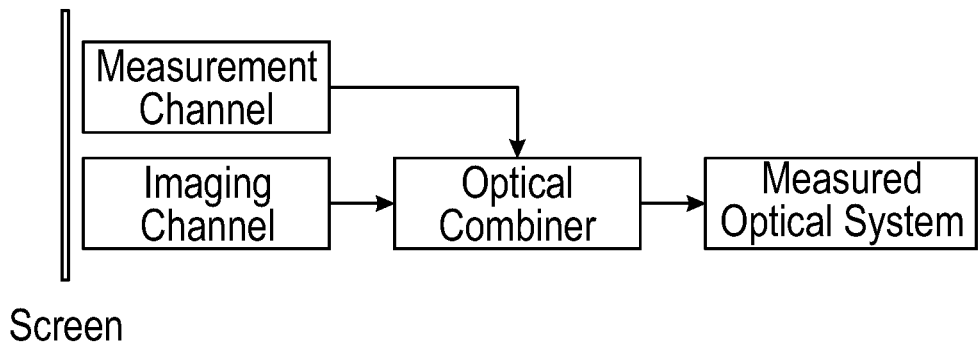

In an embodiment of the invention a screen is a source of images going through at least two channels. At least one of them is a measurement channel and at least one of them is an imaging channel. The channels are then optically overlayed upon each other by use of an optical combiner. The combined channels are then directed at a measured optical system. FIG. 4 presents a schematic representation of the proposed embodiment. In one implementation of the invention, the measurement channel is comprised of a reverse Shack-Hartman refraction measurement system. In another implementation of the proposed embodiment the measured optical system is the human eye and the imaging channel is used for accommodation mitigation. In yet another implementation, the optical combiner is for example a beamsplitter, polarizing beamsplitter, beam combiner, waveguide or fiber combiner.

Figure 5:
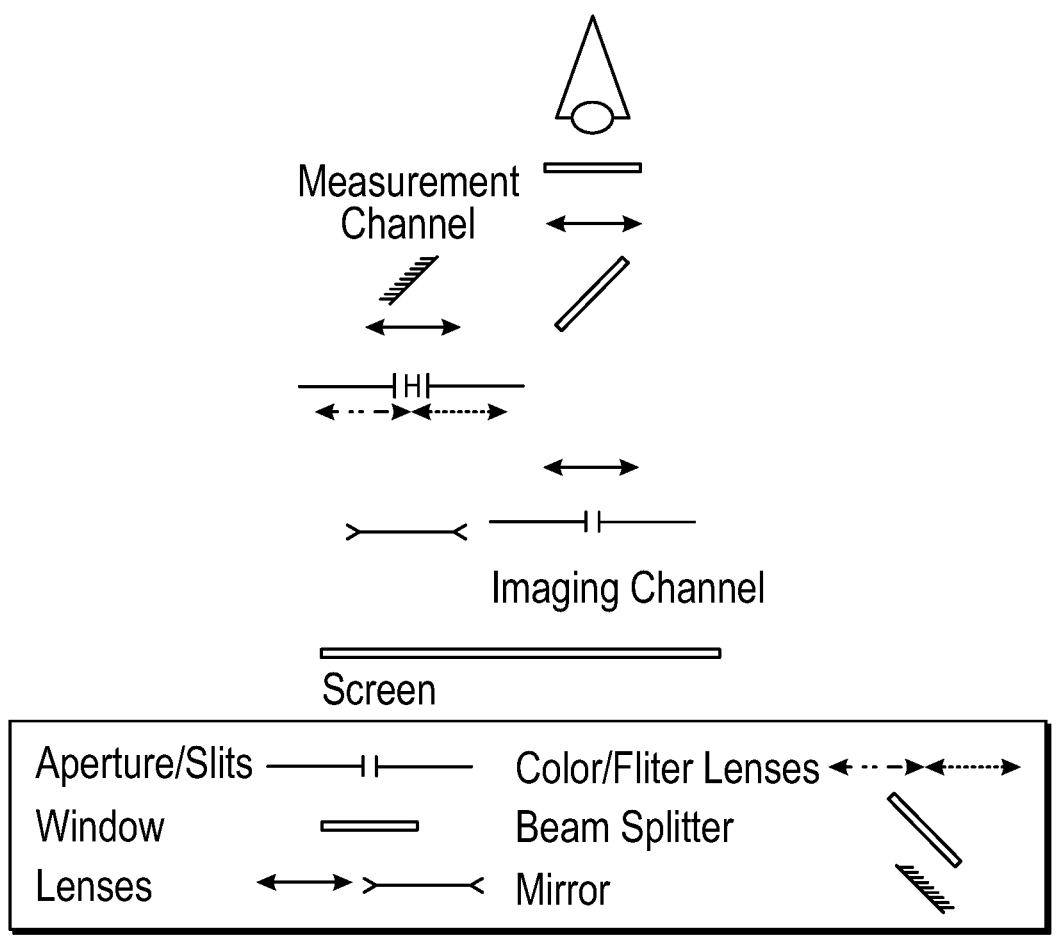

FIG. 5 presents a proposed example of an embodiment of the invention in which the use of the device is monocular. A screen is used to present images and patterns. The screen could be for example a smartphone screen. The measurement channel is comprised of a collecting lens, two color lenses and two slits as described in [PVT and VC applications], utilizing the reverse Shack-Hartmann refraction measurement method. The slits plane is then optically relayed to the user's eye. In FIG. 5 an example of the relay optics used is shows as two lenses in a 4-f configuration. This configuration allows for a common optical element with the imaging channel as well as improved tolerances and robustness. Other relay arrangements may be considered, for example, a single lens relay. The imaging channel is comprised of an aperture, a first lens close to the screen and a second lens close to the user's eye. The aperture is used to increase the depth of focus of the system, allowing people of various refractive error to use the device. The first lens, which may be an asphere, is used to collect the light from the screen and create a secondary, virtual, image plane that includes the distortion and aberrations, such that when this plane is imaged onto the user's retina by the second lens and the human eye optics, these cancel the aberrations and distortion of the optical system and the image is sharp. The two channels are combine in FIG. 5 as an example with a beamsplitter.

Figure 6:
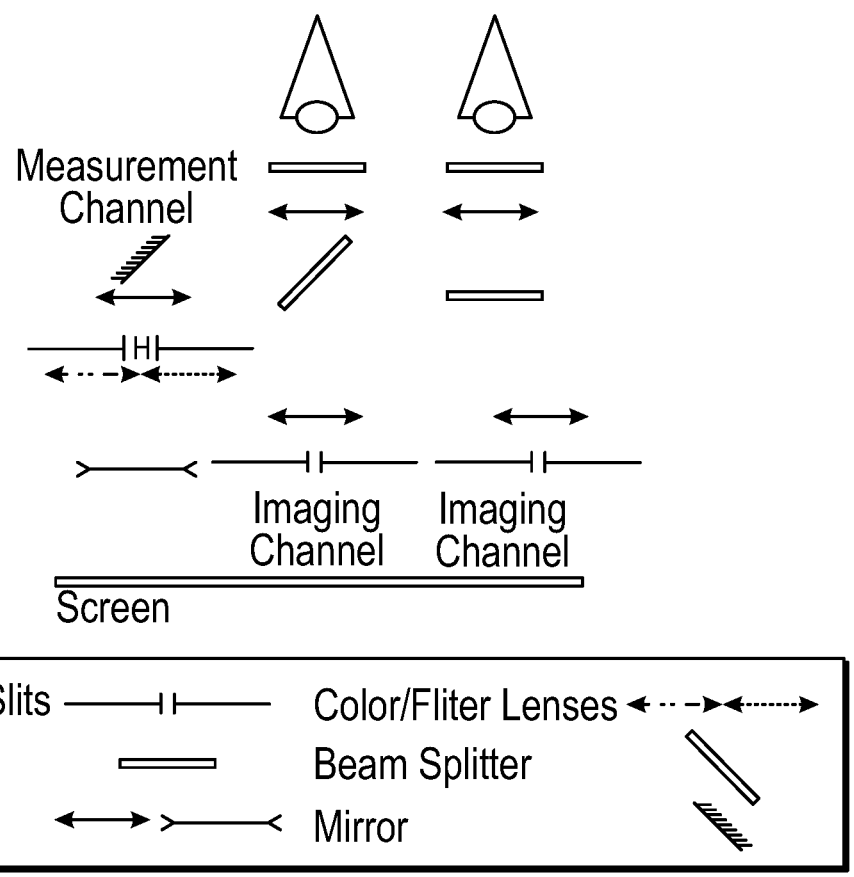

FIG. 6 proposes another embodiment of the invention where the device is binocular. This allows for better depth perception by introducing parallax and images to both eyes. Having depth perception allows for accommodation control. Having the measurement channel affixed to one eye makes the device robust while maintaining a cheap implementation. A mechanical implementation is required to allow testing of both eyes. An example of such mechanical design will be a symmetric design of the device allowing the user to flip it 180° to measure the other eye. Furthermore, proper patterns should be presented on the screen to account for the different orientation of the color lenses.

Figure 7:
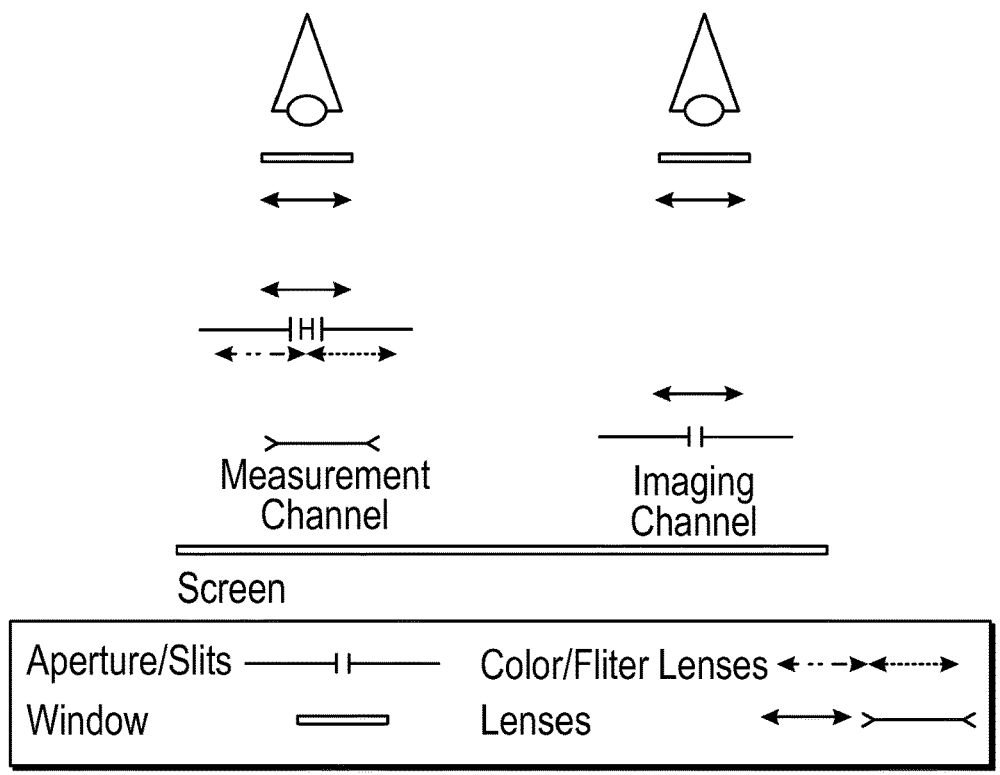
Figure 8:
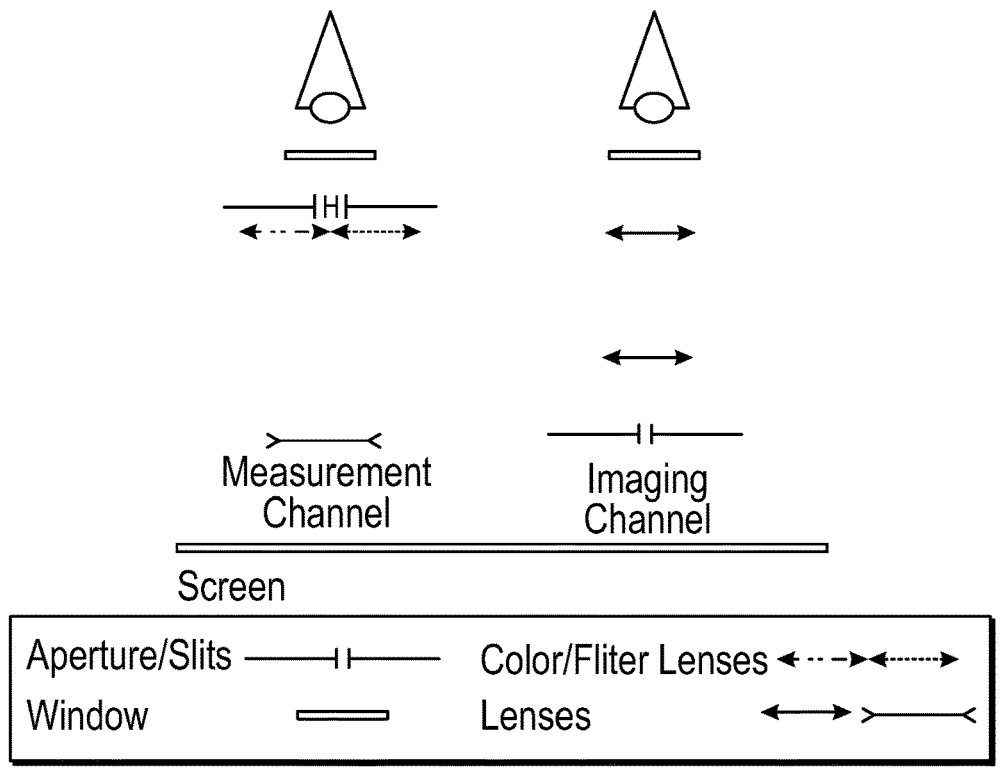

Another implementation of a monocular measurement system with a binocular form factor is presented in FIGS. 7 and 8. This implementation presents a device where the measurement channel is presented for one eye and the imaging channel is presented to the other eye. This relies on the human brain to combine the images without disparity due to lack of external reference. FIG. 7 presents an implementation with a relay system applied to the measurement channel while FIG. 8 presents an implementation without a relay system. The main difference will be in manufacturability and cost vs. performance.

Figure 9:
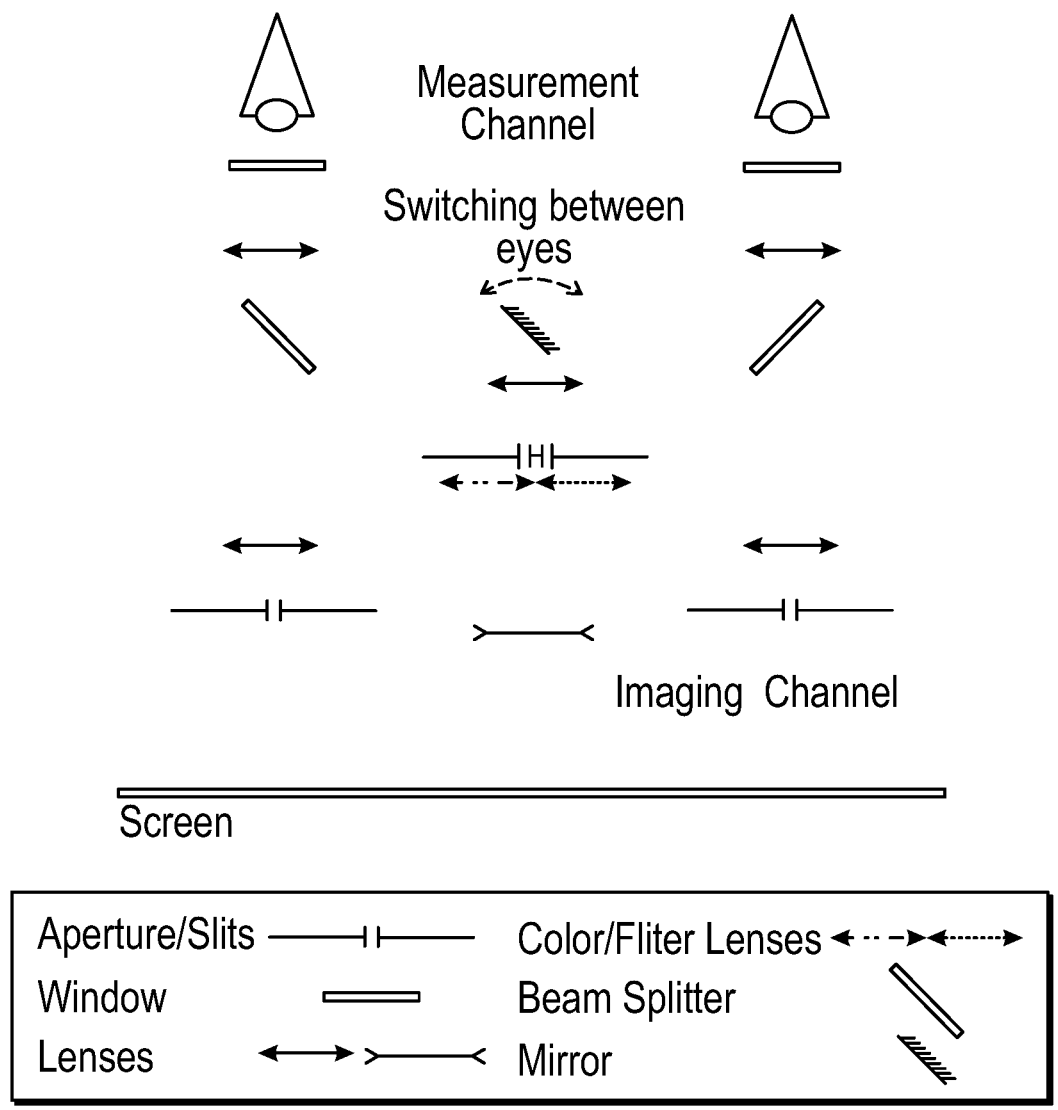

In yet another embodiment of the invention, FIG. 9 presents a binocular device that allows the user to test both eyes. A single measurement channel is shared between two imaging channels. The measurement for each eye can alternate with a mechanical mechanism, for example, flip mirror, multiple mirrors on translation (motorized or with a solenoid). Alternatively, an optical system could be implemented that splits the image to both eyes, this has a disadvantage of measuring both eyes simultaneously instead of one eye at a time. Due to the nature of this design, the measurement channel length changes with changing the pupillary distance (PD) of the user. This causes the measurement channel to greatly depend on the PD. A calibration procedure could be performed where the optical power measured in the measurement channel is tested against known optical systems and the conversion formula is also dependent on the PD.

Figure 10:
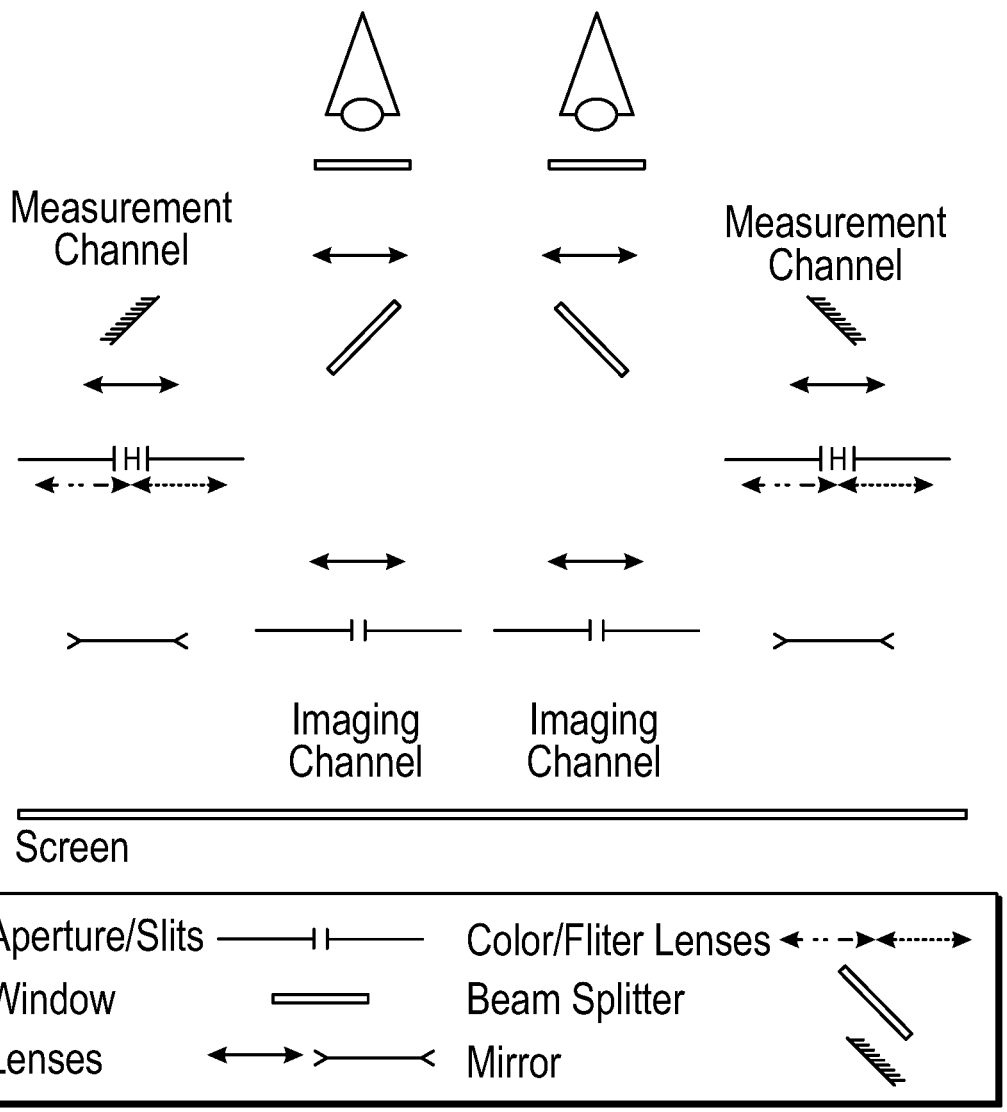
Figure 11A:
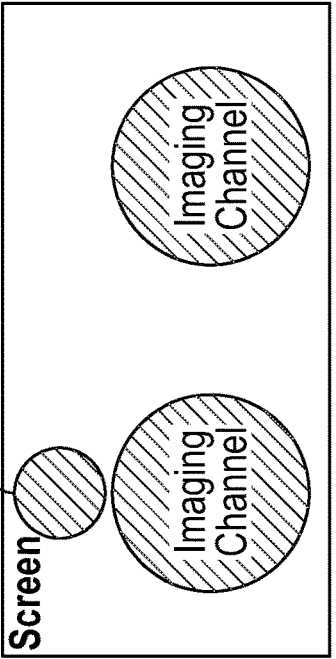
Figure 11B:
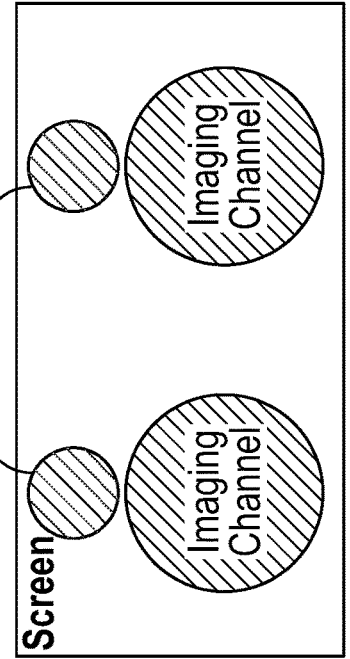
Figure 11C:
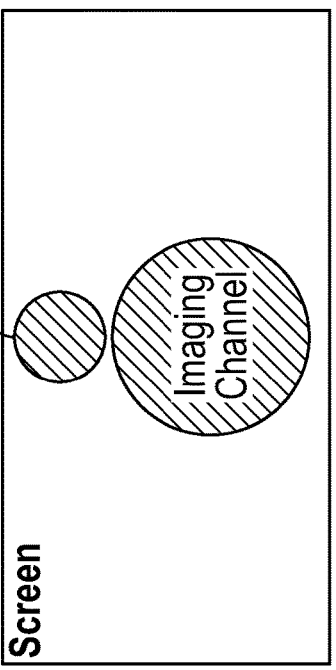
Figure 11D:
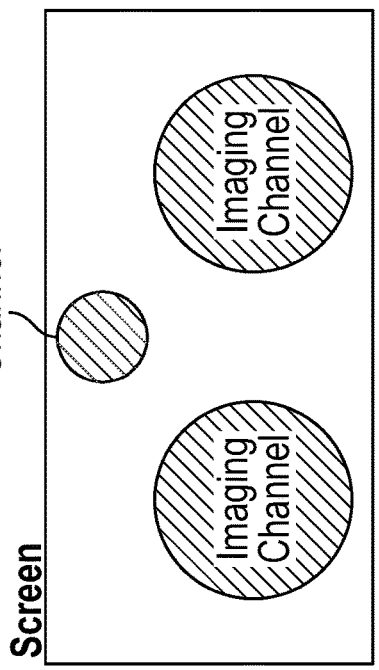

In yet another implementation of the invention, a measurement channel is attached to each imaging channel in a binocular measurement system. This implementation allows for a more robust system as there is no dependence on the PD. FIG. 10 presents an example of such implementation.

FIG. 11 presents examples of different arrangements of the channels on the screen. FIG. 11. A presents the case where there is a single measurement channel and a single imaging channel in a monocular device implementation. FIG. 11. B presents the case of a binocular device with the measurement channel attached to one eye. FIG. 11. C presents the case of a binocular device with a shared measurement channel for both eyes. FIG. 11. D presents the case of a binocular device with dedicated measurement channel for each imaging channel for each eye.

In an embodiment of the invention, a measurement channel is designed to measure the refraction of an optical system. The measurement channel is based on the reverse Shack-Hartmann concept [PVT and VC patents]. In one implementation, this measurement system comprised of a collecting lens, for example a negative lens, and asphere or another optical collecting lens, two color lenses for separating the patterns of measurement chromatically (alternative separation methods could be conceived such as polarization based separation or spatial separation with baffles for example) and two slits that create a pupil plane for the optical measurement system. In a proposed implementation of the embodiment, presented in FIG. 12, a relay system is presented in front of the measurement system. This relay system allows for the measurement system to be farther away from the measured optical system. Furthermore, building the relay system such that it images the slits onto the pupil of the measured optical system. This allows for increased field of view (FoV) due to lack of obscuration from the slits themselves that occurs with a system where the slits are places in an intermediary plane between the pupil plane and the imaging plane. Furthermore, the relay system can be used to correct for misalignment or aberrations in the measurement system to provide better optical performance for the system. In an implementation of the proposed embodiment the relay system could have magnification and could be optimized to increase the measurement resolution or to decrease the slit size on the pupil which can allow for smaller pupil sizes or allow for more robust system and easier view of the patterns.

In yet another embodiment of the invention, an imaging channel is designed to allow a user to view an image, video or other media from a screen or other display device, for example, a smartphone. The system is comprised of a first lens, for example an asphere, aimed at creating a secondary virtual image plane. The virtual image plane includes aberrations, distortion and field curvature that negate those that are present from the second lens in the system such that the image on the image plane (e.g. the retina of the eye) is sharp. This is done ideally by adapting the optical performance in a telecentric form from the screen to the secondary virtual image plane and then to the final imaging plane. The aperture in the optical system allows for adjustment of the light throughput and depth of focus. This allows the users of various refractive error to be able to view the images or other media presented sharply. Such an implementation is depicted for example in FIG. 13.

Figure 14A:
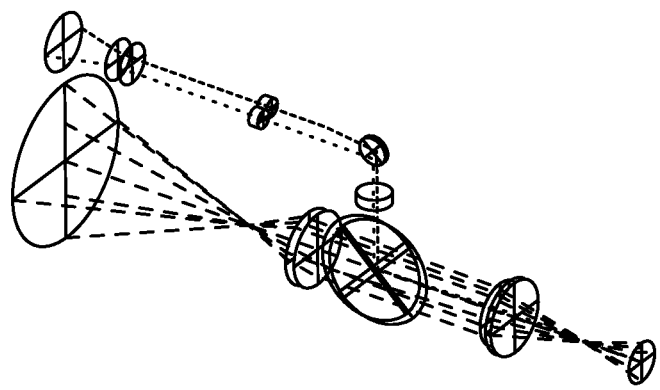
Figure 14B:
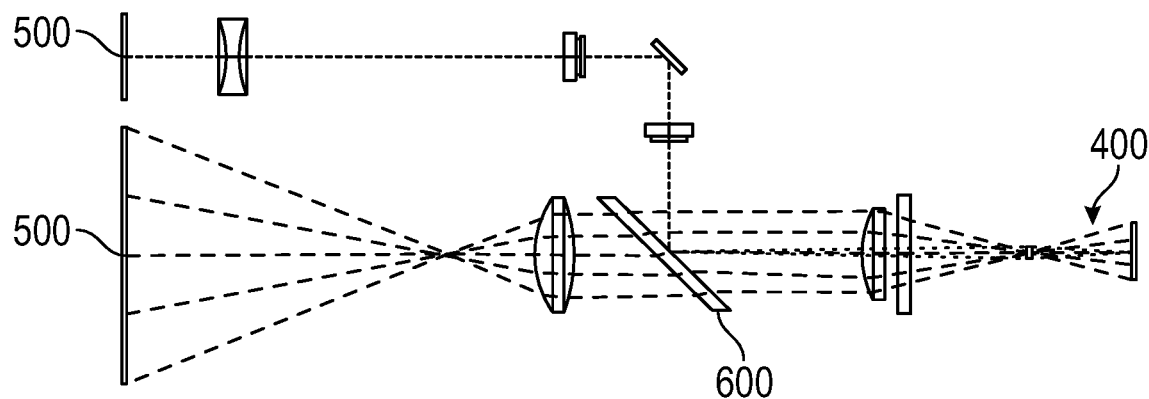
Figure 14C:
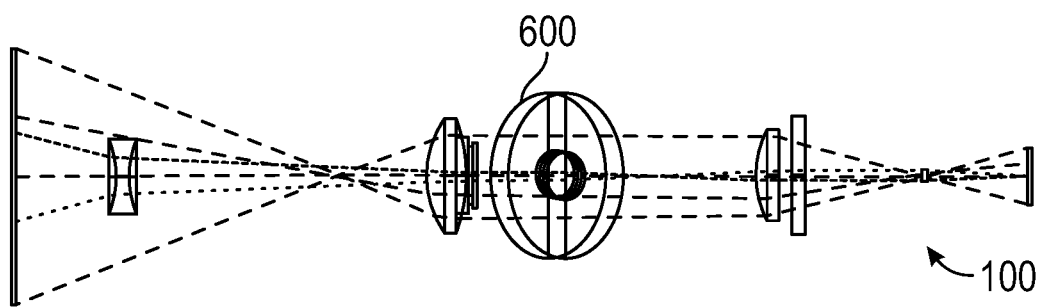

This type of imaging channel could be used in a binocular form to create a viewing device for virtual reality, augmented reality, or other media presentation (e.g. video streaming, TV watching, or gaming) for users with refractive error without the requirement of using corrective eyewear. FIG. 14 presents an example implementation of a binocular system that allows a user to view content without the need for refraction correction.

Figure 15:
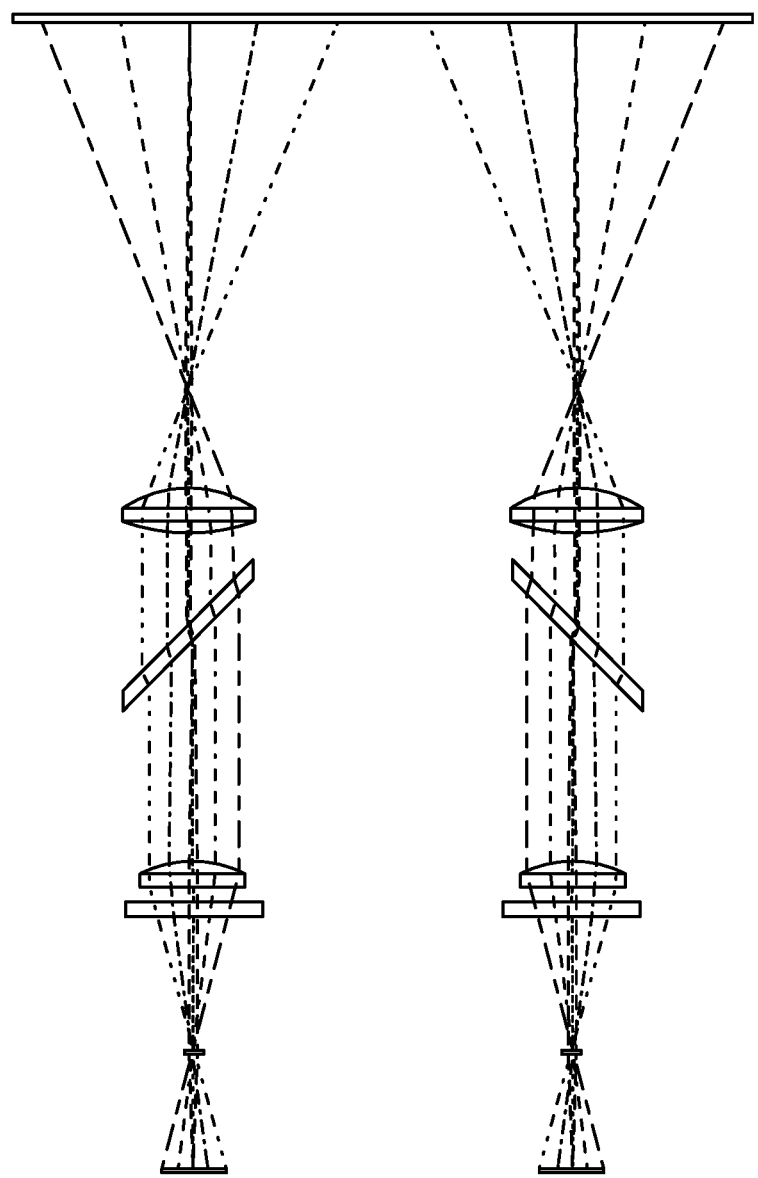
Figure 16:
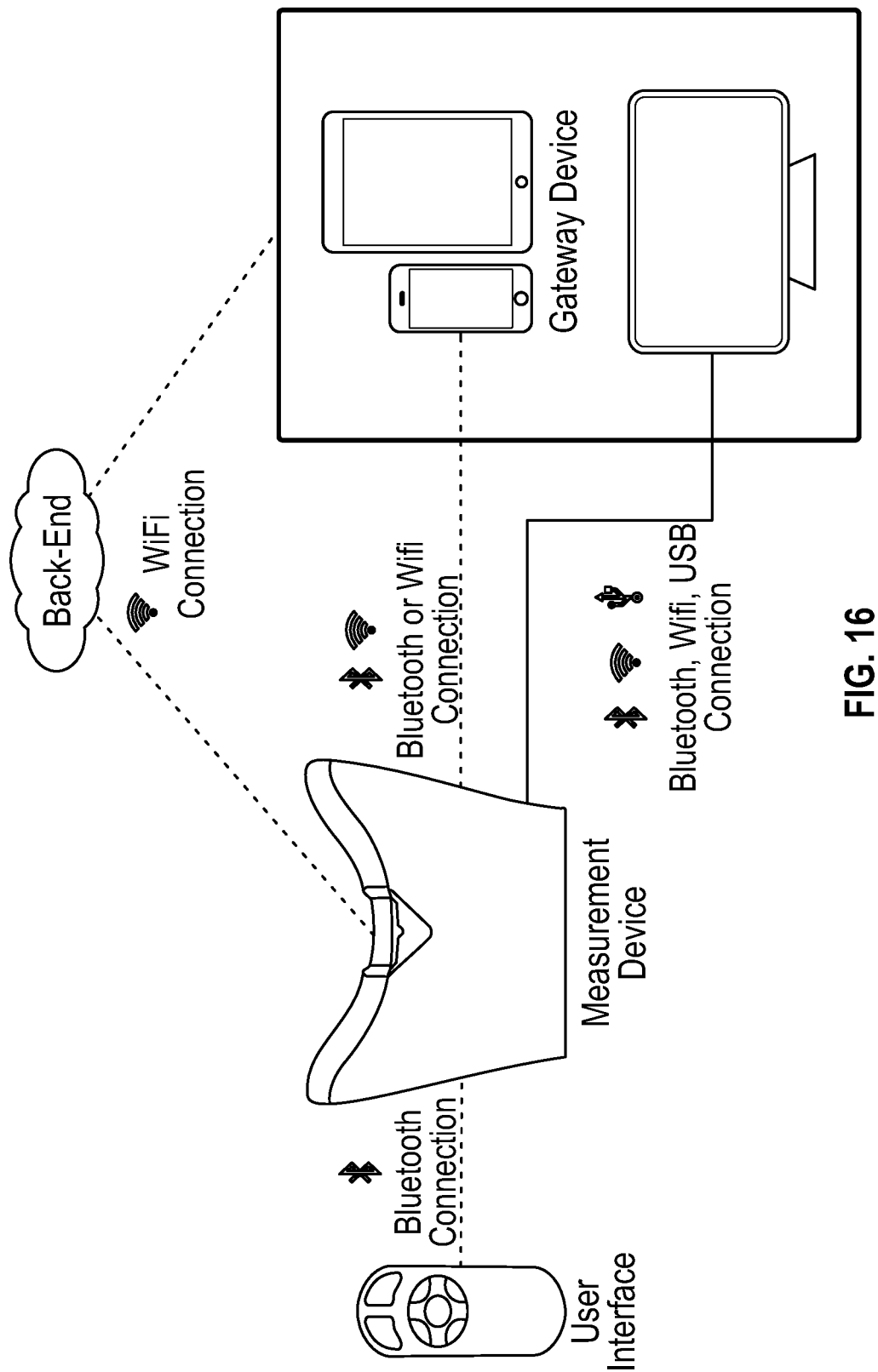

In a proposed embodiment of the invention, a measurement system is part of a complete user experience environment. FIG. 15 presents an example implementation of such environment connectivity. The environment is comprised of 4 main elements: the measurement device, a user interface device, a gateway device and a back-end. FIG. 15 shows a measurement device that connects to a user interface device through Bluetooth connection. It also connects to a gateway device through a Bluetooth, USB or WiFi connection. The back-end is connected to both the measurement device as well as the gateway device though a WiFi connection. The user interface device may be for example a controller, a joystick, a mouse, a keyboard—it allows the user to interact directly with the measurement device, especially for taking tests. It is preferred that the user interface device allows for blind interaction, i.e. without the need to see the user interface device. The gateway device could be a smartphone, a tablet or a computer. The gateway device runs a gateway application. The goal of the gateway device and application is to setup, adjust and configure the measurement device. It also enables computation and user interface for the measurement data and can serve as a passthrough of data to the back-end. The back-end is aimed at storing and aggregating measurement results. It allows for advanced analysis of the results, reporting and statistics.

Figure 17:
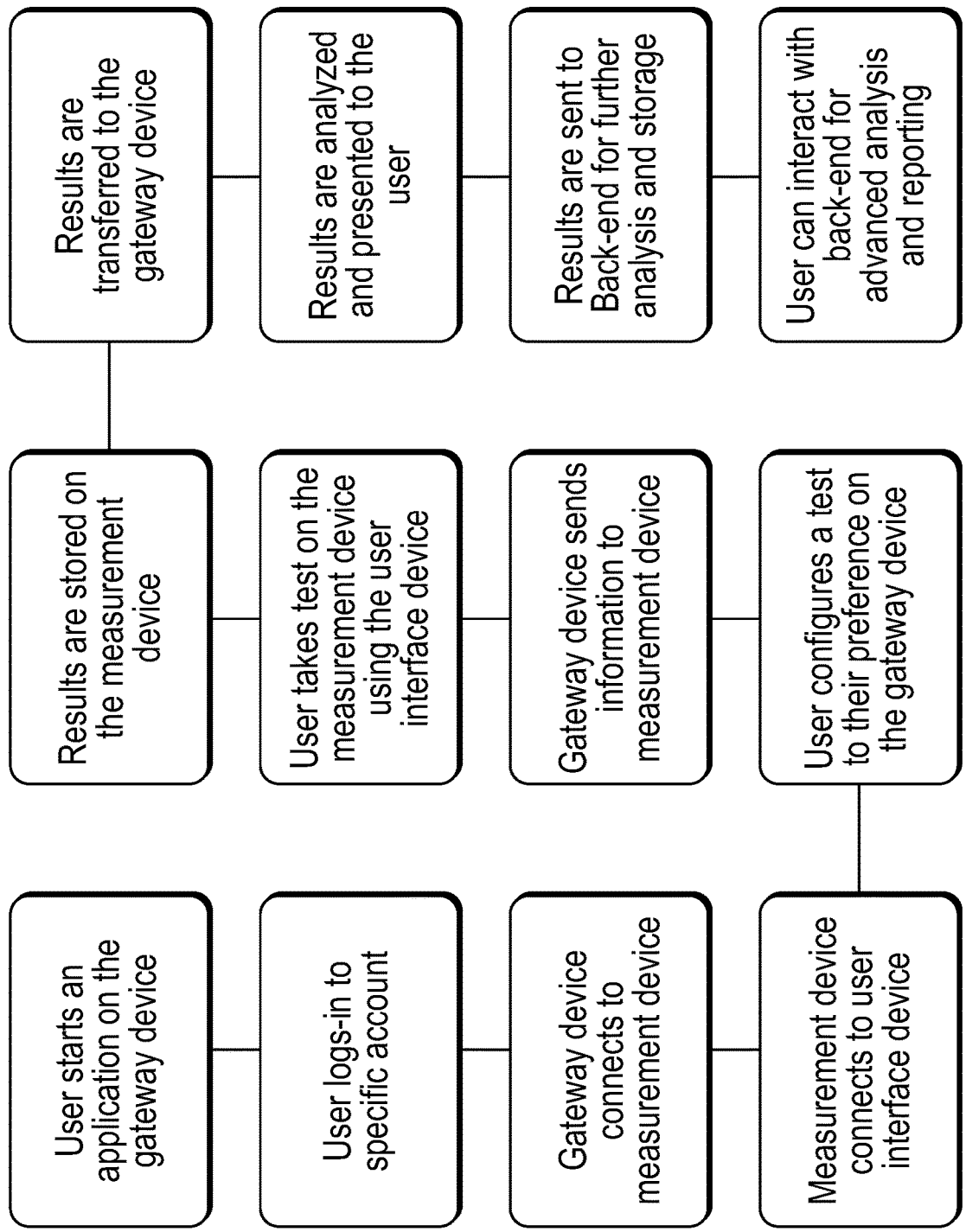

In one proposed process, presented in FIG. 17, a user starts the application on the gateway device, logs into their account or an account they have control over (e.g. enterprise, doctor, other professional). The log-in information is used to determine the access and type of tests in the device. The gateway device then connects to the measurement device. The measurement device connects to the user interface device. This could be done through or with the help of the gateway device as initial user interface device. The user then can configure a test based on the given options in the gateway application. For example, the measurement pattern, the imaging format and any potential gamification options. The gateway device then sends all the information to the measurement device. The measurement device then adjusts and configures based on the given information. These may include for example, PD adjustment, user ID to save results under, patterns and images to present during the test. The user then takes tests on the measurement device using the user interface device. Results are then stored on the measurement device. User may view their results on the gateway device. The gateway device performs analysis on the results and presents them to the user in a familiar format. The results are also sent to the backend for further analysis and storage. The user may interact with the back end to see these advanced analyses. The user may also create reports and analyze results in a more wholistic approaches.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Disclosed embodiments may include the following items.

1. A system to correct errors in an optical system, without need for corrective lenses for the optical system, the system comprising:
   an imaging channel;
   a measurement channel.

The system of 1 wherein the imaging channel and measurement channel share a common optical path.

The system of 1 comprising a monocular device and wherein the measurement channel comprises a collecting lens, two color lenses, two slits and a slits plane optically related to the optical system.

The system of 3 wherein the slits plane is optically related by use of two lenses disposed in a 4-f configuration.

The system of 1 wherein the imaging channel comprises an aperture, a first lens disposed proximal to a screen and a second disposed to the optical system.

The system of 5 wherein the aperture is configured to adjust a depth of focus of the imaging channel, allowing optical systems with refractive error to use the system.

The system of 5 wherein the first lens comprises a sphere, the first lens colleting light from a screen and the first lens using said light from the screen to create a secondary, virtual, image plane that includes distortion and aberrations, such that when said secondary, virtual image plane is imaged via the second lens onto the optical system, the aberrations and distortion of the optical system are cancelled and the image of the imaging channel is sharp.

The system of 1 wherein a beam splitter combines the imaging channel and the measurement channel.

A binocular system to measure the optical characteristics of an optical system, the system comprising:
 a measurement channel presented to a first eye; the measurement channel comprising a window, an aperture, two color and filter lenses, a third lens and a view to a screen;
 an imaging channel presented to a second eye; the imaging channel comprising a window, a first lens, a second lens, an aperture and a view to the screen.

(FIG. 12). A measurement system to measure refraction of an optical system, the measurement system comprising:
 a collecting lens, two color lenses used for separating patterns of measurement chromatically and two slits used to create a pupil plane for an optical measurement system;
 a relay optic system disposed in front of the measurement system.

The measurement system of claim 10 wherein the relay system images the slits onto a pupil of the measured optical system.

(FIG. 13) A system comprising and imaging channel allowing a user to view an image from a screen, the system comprising:
 a first lens used to create a secondary virtual image plane;
 a second lens presenting aberrations, distortion and field curvature;
 the secondary virtual image plane comprising aberrations, distortion and field curvature that negate the aberrations, distortion and field curvature of the second lens;
 an aperture allowing for adjustment of light throughput and depth of focus.

(FIG. 14) A system comprising an image channel (100) combined with a measurement channel (150) the system (700) comprising:
 the image channel comprising, a measured optical system 400 presented with a window (250) a convex lens (240) a beam splitter (600) an aspheric lens (260) and a screen (500);
 the measurement channel starting at the beam splitter, reflecting to a convex lens, a first relay lens, a slit plane (225) a pair of colored lens (220), a demagnifier lens and the screen.

A method to find errors in an optical system (400), the method comprising the combination of using an image channel (100) combined with a measurement channel (150);
 wherein the image channel uses a second relay lens, a beam splitter, an aspheric lens, an aperture and a screen;
 wherein the measurement channel continues from the beam splitter to a second optical relay lens to a slit plane to a pair of colored lens, a demaginfier and a screen.

A system (FIG. 15) of binocular form to create a viewing device for users with refractive error without need of corrective eyewear for a user, the system comprising the components of 14 used in two optical trains, one for each eye of a user.

What is claimed is:

1. A system to correct errors in an optical system, without need for corrective lenses for the optical system, the system comprising:
 a) an imaging channel;
 b) a measurement channel;
 c) a monocular device and wherein the measurement channel comprises a collecting lens, two color lenses, two slits and a slits plane optically related to the optical system and contained within the monocular device.

2. The system of claim 1 wherein the imaging channel and measurement channel share a common optical path.

3. The system of claim 1 wherein the slits plane is optically related by use of two lenses disposed in a 4-f configuration.

4. The system of claim 1 wherein the imaging channel comprises an aperture, a first lens disposed proximal to a screen and a second lens disposed within the optical system.

5. The system of claim 4 wherein the aperture is configured to adjust a depth of focus of the imaging channel, allowing optical systems with refractive error to use the system.

6. The system of claim 4 wherein the first lens comprises a sphere, the first lens colleting light from a screen and the first lens using said light from the screen to create a secondary, virtual, image plane that includes distortion and aberrations, such that when said secondary, virtual image plane is imaged via the second lens onto the optical system, the aberrations and distortion of the optical system are cancelled and the image of the imaging channel is in focus.

7. The system of claim 1 wherein a beam splitter combines the imaging channel and the measurement channel.

8. A method to find errors in an optical system, the method comprising the combination of using an image channel combined with a measurement channel;
 a) wherein the image channel uses a second relay lens, a beam splitter, an aspheric lens, an aperture and a screen;
 b) wherein the measurement channel continues from the beam splitter to a second optical relay lens to a slit plane to a pair of colored lens, a demaginfier and a screen.

9. The method of claim 8 using a binocular form to create a viewing device for users with refractive error without need of corrective eyewear for a user.

* * * * *